United States Patent
Arleth et al.

(12)

(10) Patent No.: US 6,365,715 B1
(45) Date of Patent: Apr. 2, 2002

(54) HUMAN CARDIAC/BRAIN TOLLOID-LIKE PROTEIN

(75) Inventors: Anthony J Arleth, Hatfield; Nabil A Elshourbagy, West Chester; Xiaotong Li, Devon; Robert N Willette, Pottstown, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/432,473

(22) Filed: Nov. 1, 1999

Related U.S. Application Data

(62) Division of application No. 08/991,408, filed on Dec. 16, 1997, now Pat. No. 6,008,017.
(60) Provisional application No. 60/034,471, filed on Jan. 2, 1997.

(51) Int. Cl.$^7$ ..................... C07K 14/435; C07K 14/475
(52) U.S. Cl. ....................................... 530/350; 530/399
(58) Field of Search ................................. 530/350, 399

(56) References Cited

U.S. PATENT DOCUMENTS 5,981,717 A * 11/1999 Greenspan et al. ......... 530/399

* cited by examiner

*Primary Examiner*—Marianne P. Allen
(74) *Attorney, Agent, or Firm*—William T. Han; Ratner & Prestia; William T. King

(57) ABSTRACT

HC/BTLP polypeptides and polynucleotides and methods for producing such polypeptides by recombinant techniques are disclosed. Also disclosed are methods for utilizing hC/BTLP polypeptides and polynucleotides in the design of protocols for the treatment of restenosis, atherosclerosis, congestive heart failure (CHF), chronic obstructive pulmonary disease (COPD), benign prostatic hypertrophy (BPH), nephritis, fibrosis, glomerulonephritis, gliosis, cirrhosis and anomalies of wound healing, such as keloids among others, and diagnostic assays for such conditions.

2 Claims, No Drawings

SEQUENCE LISTING

```
<160> NUMBER OF SEQ ID NOS: 4

<210> SEQ ID NO 1
<211> LENGTH: 5145
<212> TYPE: DNA
<213> ORGANISM: HOMO SAPIENS

<400> SEQUENCE: 1
cttacctgcc ctccgcccac ccgtgggccc ctagccaact tctccctgcg actgggggta      60
acaggcagtg cttgccctct ctactgtccc ggcggcatcc acatgtttcc ggacacctga     120 gcacccggt  cccgccgagg agcctccggg tggggagaag agcaccggtg ccctagccc      180 cgcacatcag cgcggaccgc ggctgcctaa cttctgggtc ccgtcccttc cttttcctcc     240
gggggaggag gatgggttg  ggaacgcttt ccccgaggat gctcgtgtgg ctggtggcct     300
cggggattgt tttctacggg gagctatggg tctgcgctgg cctcgattat gattacactt     360
ttgatgggaa cgaagaggat aaaacagaga ctatagatta caaggacccg tgtaaagccg     420
ctgtattttg gggcgatatt gccttagatg atgaagactt aaatatcttt caaatagata     480
ggacaattga ccttacgcag aacccctttg gaaaccttgg acataccaca ggtggacttg     540
gagaccatgc tatgtcaaag aagcgagggg ccctctacca acttatagac aggataagaa     600
gaattggctt tggcttggag caaaacaaca cagttaaggg aaaagtacct ctacaattct     660
```

```
cagggcaaaa tgagaaaaat cgagttccca gagccgctac atcaagaacg gaaagagtat    720
ggcctggagg cgttattcct tatgttatag gaggaaactt cactggcagc cagagagcca    780
tgttcaagca ggccatgagg cactgggaaa agcacacatg tgtgactttc atagaaagaa    840
gtgatgaaga gagttacatt gtattcacct ataggccttg tggatgctgc tcctatgtag    900
gtcggcgagg aagtggacct caggcaatct ctatcggcaa gaactgtgat aaatttggga    960
ttgttgttca tgaattgggt catgtgatag gcttttggca tgaacacaca agaccagatc   1020
gagataacca cgtaactatc ataagagaaa acatccagcc aggtcaagag tacaattttc   1080
tgaagatgga gcctggagaa gcaaactcac ttggagaaag atatgatttc gacagtatca   1140
tgcactatgc caggaacacc ttctcaaggg ggatgtttct ggataccatt ctcccctccc   1200
gtgatgataa tggcatacgt cctgcaattg gtcagcgaac ccgtctaagc aaaggagata   1260
tcgcacaggc aagaaagctg tatagatgtc cagcatgtgg agaaactcta caagaatcca   1320
atggcaacct ttcctctcca ggatttccca atggctaccc ttcttacaca cactgcatct   1380
ggagagtttc tgtgacccca ggggagaaga ttgttttaaa ttttacaacg atggatctat   1440
acaagagtag tttgtgctgg tatgactata ttgaagtaag agacgggtac tggagaaaat   1500
cacctctcct tggtagattc tgtgggggaca aattgcctga agttcttact tctacagaca   1560
gcagaatgtg gattgagttt cgtagcagca gtaattgggt aggaaaaggc tttgcagctg   1620
tctatgaagc gatctgtgga ggtgagatac gtaaaaatga aggacagatt cagtctccca   1680
attatcctga tgactatcgc ccgatgaagg aatgtgtgtg gaaaataaca gtgtctgaga   1740
gctaccacgt cgggctgacc tttcagtcct tgagattga aagacatgac aattgtgctt   1800
atgactacct ggaagttaga gatggaacca gtgaaaatag ccctttgata gggcgtttct   1860
gtggttatga caaacctgaa gacataagat ctacctccaa tactttgtgg atgaagtttg   1920
tttctgacgg aactgtgaac aaagcagggt tgctgctaa cttttttaaa gaggaagatg   1980
agtgtgccaa acctgaccgt ggaggctgtg agcagcgatg tctgaacact ctgggcagtt   2040
accagtgtgc ctgtgagcct ggctatgagc tgggcccaga cagaaggagc tgtgaagctg   2100
cttgtggtgg acttcttacc aaacttaacg gcaccataac caccccctggc tggcccaagg   2160
agtaccctcc taataagaac tgtgtgtggc aagtggttgc accaacccag tacagaatt t   2220
ctgtgaagtt tgagtttttt gaattggaag gcaatgaggt ttgcaaatat gattatgtgg   2280
agatctggag tggtctttcc tctgagtcta aactgcatgg caaattctgt ggcgctgaag   2340
tgcctgaagt gatcacatcc cagttcaaca atatgagaat tgaattcaaa tctgacaata   2400
ctgtatccaa gaagggcttc aaagcacatt ttttctcaga caaagatgaa tgctctaagg   2460
ataatggtgg atgtcagcac gaatgtgtca acacgatggg gagctacatg tgtcaatgcc   2520
gtaatggatt tgtgctacat gacaataaac atgattgcaa ggaagctgag tgtgaacaga   2580
agatccacag tccaagtggc ctcatcacca gtcccaactg gccagacaag tacccaagca   2640
ggaaagaatg cacttgggaa atcagcgcca ctcctggcca ccgaatcaaa ttagcccttta   2700
gtgaatttga gattgagcag catcaagaat gtgcttatga ccacttagaa gtatttgatg   2760
gagaaacaga aaagtcaccg attcttggac gactatgtgg caacaagata ccagatcccc   2820
ttgtggctac tggaaataaa atgtttgttc ggtttgtttc tgatgcatct gttcaaagaa   2880
aaggctttca agccacacat tctacagagt gtggcggacg attgaaagca gaatcaaaac   2940
caagagatct gtactcacat gctcagtttg gtgataacaa ctacccagga caggttgact   3000
gtgaatggct attagtatca gaacgggggct ctcgacttga attatccttc cagacatttg   3060
```

```
aagtggagga agaagcggac tgtggctatg actatgtgga gctctttgat ggtcttgatt    3120
caacagctgt ggggcttggt cgattctgtg gatccgggcc accagaagag atttattcaa    3180
ttggagattc agttttaatt catttccaca ctgatgacaa atcaacaag aagggatttc    3240 atataagata caaaagcata agatatccag ataccacaca taccaaaaaa taacaccaaa    3300
acctctgtca gaacacaaag gaatgtgcat aatggagaga agacatattt ttttttaaaac   3360 tgaagatatt ggcacaaatg ttttatacaa agagtttgaa caaaaaatcc ctgtaagacc    3420
agaattatct ttgtactaaa agagaagttt ccagcaaaac cctcatcagc attacaagga    3480
tatttgaact ccatgcttga tggtattaat aaagctggtg aaagggcatc atatacttca    3540
aggaagactc tacaagcttt tgttcacagc ttgaaataga tgcctcacaa ttcagacagt    3600
ttaattcagg aactgtgacc ctgaagtgtt cttttttgaca atttgtcaag atttagggac    3660
ataaaatgat cttgcaggtc gtaaactgga aaacagtatt ttggttgtct taggataatt    3720
gctgactttg tatcttggat acagtgtaaa ccagatccat ataaggtgaa tgtgaaatgg    3780
gagtcttctg agggtgattt gtactttcca tgtgtatgtg tgtgtctggt gtttggaaac    3840
tgggatattt cagcttcatt atttccactt gcaggccagc ttaacctctg aaacacaaat    3900
gatcttgaga ccactttagt gtacttacat ttagatgagt ttgaaatctc aatggtgtct    3960
aattattgca gttaaattct agacatcagt tctttaagtc tcagaaaacg cccagtgaat    4020
tggtaaactt agttcttttt tttggaagtg ctgccttttc acaccaaatc caagaagcct    4080
gtgatgtctt atgaacctta tgagaaaact ccgaagaggt gtgagcagga ttcttctgaa    4140
tgactgtctg gatggttcat tactcaagtt actgctgctg ctattgtctt tcctttgttg    4200
tcgatctgtt attgttgtat tattattgtt gatgttgtca tggttaatct attttttaaa    4260
attgaaatga agcagaagta ggccttgtga gaactgaaag gtctctttca tttttctctt    4320
cctgggattc attttttcaa aacacaatgc tggaaaaaaa agatttgttt ctgaaagact    4380
tcttatggtg ctattccata aacttttttt caaacaagtt tttgacccttt gagccaaccc    4440 acccgtagac tacgaatgtc tccctatggc tggtagcatt tgaagactaa agacttgtca    4500
aatatatcaa gagtatatca ttgcaagggc agcacttgtc ctgtggaaca actacttata    4560
atgccttaga attcctgcac atgatcaaac agatcctcct aaaacacacc ttttgaaatg    4620
ttgaacataa tagtgtatgt taattaacag ctctatgaag aaaatccatt tccatgactg    4680
aagcattgga tataaatatg gtgtcctgct tttttgtag aaaatgtaat ttgaggatga    4740
attttctgct ttaaaggcat gtgtgttttt aaaattaatg aatgtagatg tgtgattgtc    4800
tgagtgagtg aaactacaag aggtaaaaaa taatgggtgg ttgaaaagtt aaaatgtatg    4860
tgccaagttc tactagaatt ccatttgaaa tagcaccttc cttaggtttc atggacaaat    4920
aatgggaact tctaattttg atcaatccca ttaaaaaaag gctctttcct ttagagaaac    4980
tctattttga tgtcaatata gattactgta tgaagtagct ttgtgtctgt tacctgtcca    5040
tgagcataca acattgaata caattgggtg tattctttca gttttacaca attaaagtat    5100
acacacagat gtaaaaaaaa aaaaaaaaa aaaaaaaac tcgag                      5145
```

<210> SEQ ID NO 2
<211> LENGTH: 1013
<212> TYPE: PRT
<213> ORGANISM: HOMO SAPIENS

<400> SEQUENCE: 2

```
Met Gly Leu Gly Thr Leu Ser Pro Arg Met Leu Val Trp Leu Val Ala
 1               5                  10                  15

Ser Gly Ile Val Phe Tyr Gly Glu Leu Trp Cys Ala Gly Leu Asp
            20                  25                  30

Tyr Asp Tyr Thr Phe Asp Gly Asn Glu Glu Asp Lys Thr Glu Thr Ile
                35                  40                  45

Asp Tyr Lys Asp Pro Cys Lys Ala Ala Val Phe Trp Gly Asp Ile Ala
 50                  55                      60

Leu Asp Asp Glu Asp Leu Asn Ile Phe Gln Ile Asp Arg Thr Ile Asp
 65                  70                  75                  80

Leu Thr Gln Asn Pro Phe Gly Asn Leu Gly His Thr Thr Gly Gly Leu
                85                  90                  95

Gly Asp His Ala Met Ser Lys Lys Arg Gly Ala Leu Tyr Gln Leu Ile
                100                 105                 110

Asp Arg Ile Arg Arg Ile Gly Phe Gly Leu Glu Gln Asn Asn Thr Val
            115                 120                 125

Lys Gly Lys Val Pro Leu Gln Phe Ser Gly Gln Asn Glu Lys Asn Arg
 130                 135                 140

Val Pro Arg Ala Ala Thr Ser Arg Thr Glu Arg Val Trp Pro Gly Gly
 145                 150                 155                 160

Val Ile Pro Tyr Val Ile Gly Gly Asn Phe Thr Gly Ser Gln Arg Ala
                165                 170                 175

Met Phe Lys Gln Ala Met Arg His Trp Glu Lys His Thr Cys Val Thr
                180                 185                 190

Phe Ile Glu Arg Ser Asp Glu Glu Ser Tyr Ile Val Phe Thr Tyr Arg
            195                 200                 205

Pro Cys Gly Cys Cys Ser Tyr Val Gly Arg Arg Gly Ser Gly Pro Gln
            210                 215                 220

Ala Ile Ser Ile Gly Lys Asn Cys Asp Lys Phe Gly Ile Val Val His
 225                 230                 235                 240

Glu Leu Gly His Val Ile Gly Phe Trp His Glu His Thr Arg Pro Asp
                245                 250                 255

Arg Asp Asn His Val Thr Ile Ile Arg Glu Asn Ile Gln Pro Gly Gln
                260                 265                 270

Glu Tyr Asn Phe Leu Lys Met Glu Pro Gly Glu Ala Asn Ser Leu Gly
            275                 280                 285

Glu Arg Tyr Asp Phe Asp Ser Ile Met His Tyr Ala Arg Asn Thr Phe
 290                 295                 300

Ser Arg Gly Met Phe Leu Asp Thr Ile Leu Pro Ser Arg Asp Asn
 305                 310                 315                 320

Gly Ile Arg Pro Ala Ile Gly Gln Arg Thr Arg Leu Ser Lys Gly Asp
                325                 330                 335

Ile Ala Gln Ala Arg Lys Leu Tyr Arg Cys Pro Ala Cys Gly Glu Thr
                340                 345                 350

Leu Gln Glu Ser Asn Gly Asn Leu Ser Ser Pro Gly Phe Pro Asn Gly
            355                 360                 365

Tyr Pro Ser Tyr Thr His Cys Ile Trp Arg Val Ser Val Thr Pro Gly
 370                 375                 380

Glu Lys Ile Val Leu Asn Phe Thr Thr Met Asp Leu Tyr Lys Ser Ser
 385                 390                 395                 400

Leu Cys Trp Tyr Asp Tyr Ile Glu Val Arg Asp Gly Tyr Trp Arg Lys
            405                 410                 415

Ser Pro Leu Leu Gly Arg Phe Cys Gly Asp Lys Leu Pro Glu Val Leu
```

-continued

```
                 420                 425                 430
Thr Ser Thr Asp Ser Arg Met Trp Ile Glu Phe Arg Ser Ser Ser Asn
            435                 440                 445

Trp Val Gly Lys Gly Phe Ala Ala Val Tyr Glu Ala Ile Cys Gly Gly
450                 455                 460

Glu Ile Arg Lys Asn Glu Gly Gln Ile Gln Ser Pro Asn Tyr Pro Asp
465                 470                 475                 480

Asp Tyr Arg Pro Met Lys Glu Cys Val Trp Lys Ile Thr Val Ser Glu
            485                 490                 495

Ser Tyr His Val Gly Leu Thr Phe Gln Ser Phe Glu Ile Glu Arg His
                500                 505                 510

Asp Asn Cys Ala Tyr Asp Tyr Leu Glu Val Arg Asp Gly Thr Ser Glu
            515                 520                 525

Asn Ser Pro Leu Ile Gly Arg Phe Cys Gly Tyr Asp Lys Pro Glu Asp
530                 535                 540

Ile Arg Ser Thr Ser Asn Thr Leu Trp Met Lys Phe Val Ser Asp Gly
545                 550                 555                 560

Thr Val Asn Lys Ala Gly Phe Ala Ala Asn Phe Phe Lys Glu Glu Asp
            565                 570                 575

Glu Cys Ala Lys Pro Asp Arg Gly Gly Cys Glu Gln Arg Cys Leu Asn
                580                 585                 590

Thr Leu Gly Ser Tyr Gln Cys Ala Cys Glu Pro Gly Tyr Glu Leu Gly
            595                 600                 605

Pro Asp Arg Arg Ser Cys Glu Ala Ala Cys Gly Gly Leu Leu Thr Lys
            610                 615                 620

Leu Asn Gly Thr Ile Thr Thr Pro Gly Trp Pro Lys Glu Tyr Pro Pro
625                 630                 635                 640

Asn Lys Asn Cys Val Trp Gln Val Val Ala Pro Thr Gln Tyr Arg Ile
            645                 650                 655

Ser Val Lys Phe Glu Phe Phe Glu Leu Glu Gly Asn Glu Val Cys Lys
            660                 665                 670

Tyr Asp Tyr Val Glu Ile Trp Ser Gly Leu Ser Ser Glu Ser Lys Leu
            675                 680                 685

His Gly Lys Phe Cys Gly Ala Glu Val Pro Glu Val Ile Thr Ser Gln
    690                 695                 700

Phe Asn Asn Met Arg Ile Glu Phe Lys Ser Asp Asn Thr Val Ser Lys
705                 710                 715                 720

Lys Gly Phe Lys Ala His Phe Phe Ser Asp Lys Asp Glu Cys Ser Lys
            725                 730                 735

Asp Asn Gly Gly Cys Gln His Glu Cys Val Asn Thr Met Gly Ser Tyr
            740                 745                 750

Met Cys Gln Cys Arg Asn Gly Phe Val Leu His Asp Asn Lys His Asp
    755                 760                 765

Cys Lys Glu Ala Glu Cys Glu Gln Lys Ile His Ser Pro Ser Gly Leu
770                 775                 780

Ile Thr Ser Pro Asn Trp Pro Asp Lys Tyr Pro Ser Arg Lys Glu Cys
785                 790                 795                 800

Thr Trp Glu Ile Ser Ala Thr Pro Gly His Arg Ile Lys Leu Ala Phe
            805                 810                 815

Ser Glu Phe Glu Ile Glu Gln His Gln Glu Cys Ala Tyr Asp His Leu
            820                 825                 830

Glu Val Phe Asp Gly Glu Thr Glu Lys Ser Pro Ile Leu Gly Arg Leu
            835                 840                 845
```

```
Cys Gly Asn Lys Ile Pro Asp Pro Leu Val Ala Thr Gly Asn Lys Met
    850                 855                 860

Phe Val Arg Phe Val Ser Asp Ala Ser Val Gln Arg Lys Gly Phe Gln
865                 870                 875                 880

Ala Thr His Ser Thr Glu Cys Gly Gly Arg Leu Lys Ala Glu Ser Lys
                885                 890                 895

Pro Arg Asp Leu Tyr Ser His Ala Gln Phe Gly Asp Asn Asn Tyr Pro
            900                 905                 910

Gly Gln Val Asp Cys Glu Trp Leu Leu Val Ser Glu Arg Gly Ser Arg
        915                 920                 925

Leu Glu Leu Ser Phe Gln Thr Phe Glu Val Glu Glu Ala Asp Cys
    930                 935                 940

Gly Tyr Asp Tyr Val Glu Leu Phe Asp Gly Leu Asp Ser Thr Ala Val
945                 950                 955                 960

Gly Leu Gly Arg Phe Cys Gly Ser Gly Pro Pro Glu Glu Ile Tyr Ser
                965                 970                 975

Ile Gly Asp Ser Val Leu Ile His Phe His Thr Asp Asp Thr Ile Asn
            980                 985                 990

Lys Lys Gly Phe His Ile Arg Tyr Lys Ser Ile Arg Tyr Pro Asp Thr
        995                 1000                1005

Thr His Thr Lys Lys
    1010

<210> SEQ ID NO 3
<211> LENGTH: 3690
<212> TYPE: DNA
<213> ORGANISM: HOMO SAPIENS

<400> SEQUENCE: 3
gaattcggca cgagctcgtg ccgctcgtgc cgcgggtact ggagaaaatc acctctcctt      60
gattctgtgg ggacaaattg cctgaagttc ttacttctac agacagcaga atgtggattg    120
agtttcgtag cagcagtaat tgggtaggaa aaggctttgc agctgtctat gaagcgatct    180
gtggaggtga gatacgtaaa aatgaaggac agattcagtc tcccaattat cctgatgact    240
atcgcccgat gaaagaatgt gtgtggaaaa taacagtgtc tgagagctac cacgtcgggc    300
tgacctttca gtcctttgag attgaaagac atgacaattg tgcttatgac tacctggaag    360
ttagagatgg aaccagtgaa aatagcccct tgatagggcg tttctgtggt tatgacaaac    420
ctgaagacat aagatctacc tccaatactt tgtggatgaa gtttgtttct gacggaactg    480
tgaacaaagc agggtttgct gctaactttt taaagaggaa agatgagtgt gccaaacctg    540
accgtggagg ctgtgagcag cgatgtctga acactctggg cagttaccag tgtgcctgtg    600
agcctggcta tgagctgggc ccagacagaa ggagctgtga agctgcttgt ggtggacttc    660
ttaccaaact taacggcacc ataaccaccc ctggctggcc caaggagtac cctcctaata    720
agaactgtgt gtggcaagtg gttgcaccaa cccagtacag aatttctgtg aagtttgagt    780
tttttgaatt ggaaggcaat gaagtttgca aatatgatta tgtggagatc tggagtggtc    840
tttcctctga gtctaaactg catggcaaat tctgtggcgc tgaagtgcct gaagtgatca    900
catcccagtt caacaatatg agaattgaat tcaaatctga caatactgta tccaagaagg    960
gcttcaaagc acatttttttc tcagacaaag atgaatgctc taaggataat ggtggatgtc   1020
agcacgaatg tgtcaacacg atgggagct acatgtgtca atgccgtaat ggatttgtgc    1080
tacatgacaa taaacatgat tgcaaggaag ctgagtgtga acagaagatc cacagtccaa   1140
```

-continued

```
gtggcctcat caccagtccc aactggccag acaagtaccc aagcaggaaa gaatgcactt    1200
gggaaatcag cgccactcct ggccaccgaa tcaaattagc ctttagtgaa tttgagattg    1260
agcagcatcg ggaatgtgct tatgaccact tagaagtatt tgatggagaa acagaaaagt    1320
caccgattct tggacgacta tgtggcaaca agataccaga tccccttgtg gctactggaa    1380
ataaaatgtt tgttcggttt gtttctgatg catctgttca aagaaaaggc tttcaagcca    1440
cacattctac agagtgtggc ggacgattga agcagaatc aaaaccaaga gatctgtact    1500
cacatgctca gtttggtgat aacaactacc caggacaggt tgactgtgaa tggctattag    1560
tatcagaacg gggctctcga cttgaattat ccttccagac atttgaagtg gaggaagaag    1620
cagactgtgg ctatgactat gtggagctct ttgatggtct tgattcaaca gctgtggggc    1680
ttggtcgatt ctgtggatcc gggccaccag aagagattta ttcaattgga gattcagttt    1740
taattcattt ccacactgat gacacaatca acaagaaggg atttcatata agatacaaaa    1800
gcataagata tccagatacc acacatacca aaaaataaca ccaaaacctc tgtcagaaca    1860 caaggaatg tgcataatgg agagaagaca tatttttttt aaaactgaag atattggcac    1920
aaatgtttta tacaaagagt ttgaacaaaa atccctgta agaccagaat tatctttgta    1980
ctaaaagaga agtttccagc aaaaccctca tcagcattac aaggatattt gaactccatg    2040
cttgatggta ttaataaagc tggtgaaagg gcatcatata cttcaaggaa gactctacaa    2100
gcttttgttc acagcttgaa atagatgcct cacaattcag acagtttaat tcaggaactg    2160
tgaccctgaa gtgttctttt tgacaatttg tcaagattta gggacataaa atgatcttgc    2220
aggtcgtaaa ctggaaaaca gtattttggt tgtcttagga taattgctga ctttgtatct    2280
tggatacagt gtaaaccaga tccatataag gtgaatgtga atgggagtc ttctgagggt    2340 gatttgtact ttccatgtgt atgtgtgtgt ctggtgtttg gaaactggga tatttcagct    2400
tcattatttc cacttgcagg ccagcttaac ctctgaaaca caaatgatct tgagaccact    2460
ttagtgtact tacatttaga tgagtttgaa atctcaatgg tgtctaatta ttgcagttaa    2520
attctagaca tcagttcttt aagtctcaga aaacgcccag tgaattggta aacttagttc    2580
ttttttttgg aagtgctgcc ttttcacacc aaatccaaga agcctgtgat gtcttatgaa    2640
ccttatgaga aaactccgaa gaggtgtgag caggattctt ctgaatgact gtctggatgg    2700
ttcattactc aagttactgc tgctgctatt gtctttcctt tgttgtcgat ctgttattgt    2760
tgtattatta ttgttgatgt tgtcatggtt aatctatttt ttaaaattga aatgaagcag    2820
aagtaggcct tgtgagaact gaaggtctc tttcattttt ctcttcctgg gattcatttt    2880
ttcaaaacac aatgctggaa aaaaagatt tgttctgaa agacttctta tggtgctatt    2940
ccataaactt tttttcaaac aagttttga cctttgagcc aacccacccg tagactacga    3000
atgtctccct atggctggta gcatttgaag actaaagact tgtcaaatat atcaagagta    3060
tatcattgca agggcagcac ttgtcctgtg gaacaactac ttataatgcc ttagaattcc    3120
tgcacatgat caaacagatc ctcctaaaac acaccttttg aaatgttgaa cataatagtg    3180
tatgttaatt aacagctcta tgaagaaaat ccatttccat gactgaagca ttggatataa    3240
atatggtgtc ctgctttttt tgtagaaaat gtaatttgag gatgaatttt ctgctttaaa    3300
ggcatgtgtg ttttttaaaat taatgaatgt agatgtgtga ttgtctgagt gagtgaaact    3360
acaagaggta aaaaataatg ggtggttgaa aagttaaaat gtatgtgcca agttctacta    3420
gaattccatt tgaaatagca ccttccttag gtttcatgga caaataatgg gaacttctaa    3480
```

-continued

```
ttttgatcaa tcccattaaa aaaggctct ttcctttaga gaaactctat tttgatgtca    3540
atatagatta ctgtatgaag tagctttgtg tctgttacct gtccatgagc atacaacatt    3600
gaatacaatt gggtgtattc tttcagtttt acacaattaa agtatacaca cagatgtaaa    3660
aaaaaaaaaa aaaaaaaaaa aaaactcgag                                     3690
```

<210> SEQ ID NO 4
<211> LENGTH: 591
<212> TYPE: PRT
<213> ORGANISM: HOMO SAPIENS

<400> SEQUENCE: 4

```
Phe Cys Gly Asp Lys Leu Pro Glu Val Leu Thr Ser Thr Asp Ser Arg
 1               5                  10                  15

Met Trp Ile Glu Phe Arg Ser Ser Asn Trp Val Gly Lys Gly Phe
            20                  25                  30

Ala Ala Val Tyr Glu Ala Ile Cys Gly Gly Ile Arg Lys Asn Glu
        35                  40                  45

Gly Gln Ile Gln Ser Pro Asn Tyr Pro Asp Asp Tyr Arg Pro Met Lys
 50                  55                  60

Glu Cys Val Trp Lys Ile Thr Val Ser Glu Ser Tyr His Val Gly Leu
 65                  70                  75                  80

Thr Phe Gln Ser Phe Glu Ile Glu Arg His Asp Asn Cys Ala Tyr Asp
                85                  90                  95

Tyr Leu Glu Val Arg Asp Gly Thr Ser Glu Asn Ser Pro Leu Ile Gly
            100                 105                 110

Arg Phe Cys Gly Tyr Asp Lys Pro Glu Asp Ile Arg Ser Thr Ser Asn
        115                 120                 125

Thr Leu Trp Met Lys Phe Val Ser Asp Gly Thr Val Asn Lys Ala Gly
130                 135                 140

Phe Ala Ala Asn Phe Phe Lys Glu Glu Asp Glu Cys Ala Lys Pro Asp
145                 150                 155                 160

Arg Gly Gly Cys Glu Gln Arg Cys Leu Asn Thr Leu Gly Ser Tyr Gln
                165                 170                 175

Cys Ala Cys Glu Pro Gly Tyr Glu Leu Gly Pro Asp Arg Arg Ser Cys
            180                 185                 190

Glu Ala Ala Cys Gly Gly Leu Leu Thr Lys Leu Asn Gly Thr Ile Thr
        195                 200                 205

Thr Pro Gly Trp Pro Lys Glu Tyr Pro Pro Asn Lys Asn Cys Val Trp
210                 215                 220

Gln Val Val Ala Pro Thr Gln Tyr Arg Ile Ser Val Lys Phe Glu Phe
225                 230                 235                 240

Phe Glu Leu Glu Gly Asn Glu Val Cys Lys Tyr Asp Tyr Val Glu Ile
                245                 250                 255

Trp Ser Gly Leu Ser Ser Glu Ser Lys Leu His Gly Lys Phe Cys Gly
            260                 265                 270

Ala Glu Val Pro Glu Val Ile Thr Ser Gln Phe Asn Asn Met Arg Ile
        275                 280                 285

Glu Phe Lys Ser Asp Asn Thr Val Ser Lys Lys Gly Phe Lys Ala His
        290                 295                 300

Phe Phe Ser Asp Lys Asp Glu Cys Ser Lys Asp Asn Gly Gly Cys Gln
305                 310                 315                 320

His Glu Cys Val Asn Thr Met Gly Ser Tyr Met Cys Gln Cys Arg Asn
                325                 330                 335
```

```
Gly Phe Val Leu His Asp Asn Lys His Asp Cys Lys Glu Ala Glu Cys
            340                 345                 350

Glu Gln Lys Ile His Ser Pro Ser Gly Leu Ile Thr Ser Pro Asn Trp
            355                 360                 365

Pro Asp Lys Tyr Pro Ser Arg Lys Glu Cys Thr Trp Glu Ile Ser Ala
            370                 375                 380

Thr Pro Gly His Arg Ile Lys Leu Ala Phe Ser Glu Phe Glu Ile Glu
385                 390                 395                 400

Gln His Arg Glu Cys Ala Tyr Asp His Leu Glu Val Phe Asp Gly Glu
                    405                 410                 415

Thr Glu Lys Ser Pro Ile Leu Gly Arg Leu Cys Gly Asn Lys Ile Pro
            420                 425                 430

Asp Pro Leu Val Ala Thr Gly Asn Lys Met Phe Val Arg Phe Val Ser
            435                 440                 445

Asp Ala Ser Val Gln Arg Lys Gly Phe Gln Ala Thr His Ser Thr Glu
450                 455                 460

Cys Gly Gly Arg Leu Lys Ala Glu Ser Lys Pro Arg Asp Leu Tyr Ser
465                 470                 475                 480

His Ala Gln Phe Gly Asp Asn Asn Tyr Pro Gly Gln Val Asp Cys Glu
                    485                 490                 495

Trp Leu Leu Val Ser Glu Arg Gly Ser Arg Leu Glu Leu Ser Phe Gln
            500                 505                 510

Thr Phe Glu Val Glu Glu Ala Asp Cys Gly Tyr Asp Tyr Val Glu
            515                 520                 525

Leu Phe Asp Gly Leu Asp Ser Thr Ala Val Gly Leu Gly Arg Phe Cys
            530                 535                 540

Gly Ser Gly Pro Pro Glu Glu Ile Tyr Ser Ile Gly Asp Ser Val Leu
545                 550                 555                 560

Ile His Phe His Thr Asp Asp Thr Ile Asn Lys Lys Gly Phe His Ile
                    565                 570                 575

Arg Tyr Lys Ser Ile Arg Tyr Pro Asp Thr Thr His Thr Lys Lys
            580                 585                 590
```

HUMAN CARDIAC/BRAIN TOLLOID-LIKE PROTEIN

This application is a division of U.S. application Ser. No. 08/991,408, filed Dec. 16, 1997, now U.S. Pat. No. 6,008,017 which claims the benefit of U.S. Provisional Application No. 60/034,471, filed Jan. 2, 1997, both of whose contents are incorporated herein by reference in their entireties.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the astacin protein family, hereinafter referred to as human cardiac/brain tolloid-like protein (hC/BTLP). The invention also relates to inhibiting or activating the action of such polynucleotides and polypeptides.

BACKGROUND OF THE INVENTION

The hC/BTLP gene appears to possess all of the important protein domains present in the bone morphogenetic protein (BMP)-1/procollagen C-proteinase (PCP) protein. Members of the astacin family of metalloproteinases, such as BMP-1, have previously been linked to cell differentiation and pattern formation during development through a proposed role in the activation of latent growth factors of the TGF-β superfamily. In addition, recent findings indicate that BMP-1 is identical to PCP, which is a metalloproteinase involved in the synthesis of matrix collagen. This observation suggests that a functional link may exist between astacin metalloproteinases, growth factors and cell differentiation and pattern formation during development, as well as fibrotic processes characterized by the accumulation of matrix collagen.

Nucleotide and amino acid sequence homologues suggest that hC/BTLP, like BMP-1, possesses PCP activity. PCP activity is one of the essential enzymatic steps required for the extracellular production of insoluble collagen fibrils from soluble procollagen. However, mouse mammalian tolloid-like protein is the most closely related homologues of hC/BTlP. Mouse mammalian tolloid-like protein and BMP-1 are distinct gene products with differential tissue distribution. Based on cross-species comparisons, the regulation and distribution of hC/BTlP would be expected to be distinct from BMP-1. Indeed, mouse mammalian tolloid-like protein exhibits a unique tissue distribution when compared to BMP-1. Thus, the selective inhibition of matrix collagen accumulation is important in highly localized fibrotic disorders, e.g., gliosis associated with neurotrauma and ventricular fibrosis associated with congestive heart failure. This indicates that the astacin protein family has an established, proven history as therapeutic targets.

Clearly there is a need for identification and characterization of further members of the astacin protein family which can play a role in preventing, ameliorating or con g dysfunctions or diseases, including, but not limited to, restenosis, atherosclerosis, congestive heart failure (CHF), chronic obstructive pulmonary disease (COPD), benign prostatic hypertrophy (BPH), nephritis, fibrosis, glomerulonephritis, gliosis, cirrhosis and anomalies of wound healing, such as keloids, among others.

SUMMARY OF THE INVENTION

In one aspect, the invention relates to hC/BTLP polypeptides and recombinant materials and methods for their production. Another aspect of the invention relates to methods for using such hC/BTLP polypeptides and polynucleotides. Such uses include the treatment of restenosis, atherosclerosis, congestive heart failure (CHF), chronic obstructive pulmonary disease (COPD), benign prostatic hypertrophy (BPH), nephritis, fibrosis, glomenulonephritis, gliosis, cirrhosis and anomalies of wound healing, such as keloids, among others. In still another aspect, the invention relates to methods to identify agonists and antagonists using the materials provided by the invention, and treating conditions associated with hC/BTLP imbalance with the identified compounds. Yet another aspect of the invention relates to diagnostic assays for detecting diseases associated with inappropriate hC/BTLP activity or levels.

DESCRIPTION OF THE INVENTION

Definitions

The following definitions are provided to facilitate understanding of certain terms used frequently herein.

"HC/BTLP" refers, among others, generally to a polypeptide having the amino acid sequence set forth in SEQ ID NO:2 or an allelic variant thereof.

"HC/BTLP activity or hC/BTLP polypeptide activity" or "biological activity of the hC/BTLP or hC/BTLP polypeptide" refers to the metabolic or physiologic function of said hC/BTLP including similar activities or improved activities or these activities with decreased undesirable sideffects. Also included are antigenic and immunogenic activities of said hC/BTLP.

"HC/BTLP gene" refers to a polynucleotide having the nucleotide sequence set forth in SEQ ID NO:1 or allelic variants thereof and/or their complements.

"Antibodies" as used he rein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RENA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene encoded amino acids. "Polypeptides" include amino acid sequences modified either by natural processes, such as post translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-lining, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post translational Protein Modifications: Perspectives and Prospects, pgs. 1–12 in POST TRANSLATIONAL COVALENT MODIFICATION OF PROTEINS, B. C. Johnson, Ed., Academic Press, New York, 1983; Seifter et al, "Analysis for protein modifications and nonprotein cofactors", *Meth Enzymol* (1990) 182:626–646 and Rattan et al., "Protein Synthesis: Post translational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g. (COMPUTATIONAL MOLECULAR BIOLOGY, Lesk, A. M., ed., Oxford University Press, New York, 1988; BIOCOMPUTING: INFORMATION AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER. Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., SIAM *J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., SIAM *J Applied Math* (1988) 48:1073. Methods to determine identity and similarity are codified in computer programs. Preferred computer program methods to determine identity and similarity between two sequences include, but are not limited to, GCS program package (Devereux, J., et al, *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to hC/BTLP polypeptides (or hC/BTLP proteins). The hC/BTLP polypeptides include the polypeptide of SEQ ID NOS:2 and 4; as well as polypeptides comprising the amino acid sequence of SEQ ID NO: 2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within hC/BTLP polypeptides are polypeptides having the amino acid sequence which have at least 80% identity to the polypeptide having the amino acid sequence of SEQ ID NO.2 over its entire length, and still more preferably at least 90% identity, and still more preferably at least 95% identity to SEQ ID NO:2. Furthermore, those with at least 97–99% are highly preferred. Preferably hC/BTLP polypeptide exhibit at least one biological activity of hC/BTLP.

The hC/BTLP polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the hC/BTLP polypeptides are also included in the invention. A fragment is a polypeptide having an amino acid sequence that entirely is the same as part, but not all, of the amino acid sequence of the aforementioned hC/BTLP polypeptides. As with hC/BTLP polypeptides, fragments may be "free-standing," or comprised within a larger polypeptide of which they form a part or region, most preferably as a single continuous region. Representative examples of polypeptide fragments of the invention, include, for example, fragments from about amino acid numbers 1–20, 21–40, 41–60, 61–80, 81–100, and 101 to the end of hC/BTLP polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of hC/BTLP polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and tum-forming regions, coil and coil-forming regions, hydrophilic regions, hydrophobic regions, alpha amphipathic regions, beta amphipathic regions, flexible regions, suit-forming regions, substrate binding region, and high antigenic index regions. Other preferred fragments are biologically active fragments. Biologically active fragents are those that mediate hC/BTLP activity, including those with a similar activity or an improved activity, or with a decreased undesirable activity. Also included are those that are antigenic or immunogenic in an animal, especially in a human.

Preferably, all of these polypeptide fragments retain the biological activity of the hC/BTLP, including antigenic activity. Among the most preferred frEment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or arornatic residues Phe and Tyr. Particularly preferred are variants in which several, 5–10, 1–5, or 1–2 amino acids are substituted, deleted, or added in any combination.

The hC/BTLP polypeptides of the invention can be prepared in any suitable marmer. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention reltes to hC/BTLP polynucleotides. hC/BTLP polynucleotides include isolated polynucleotides which encode the hC/BTLP polypeptides and fragments, and polynucleotides closely related thereto. More specifically, hC/BTLP polynucleotide of the invention include a polynucleotide comprising the nucleotide sequence contained in SEQ ID NO: 1 encoding a hC/BTLP polypeptide of SEQ ID NO: 2, and polynucleotides having the particular sequences of SEQ ID NOS: 1 and 3. hC/BTLP polynucleotides further include a polynucleotide comprising a nucleotide sequence that has at least 80% identity over its entire length to a nucleotide sequence encoding the hC/BTLP polypeptide of SEQ ID NO:2, and a polynucleotide comprising a nucleotide sequence that is at least 80% identical to that of SEQ ID NO: 1 over its entire length. In this regard, polynucleotides at least 90% identical are particularly preferred, and those with at least 95% are especially preferred. Futhermore, those with at least 97% are highly preferred and those with at least 98–99% are most highly preferred with at least 99% being the most preferred. Also included under hC/BTLP polynucleotides are a nucleotide sequence which has sufficient identity to a nucleotide sequence contained in SEQ ID No: 1 to hybridize under conditions useable for amplification or for use as a probe or marker. The invention also provides polynucleotides which are complementary to such hC/BTLP polynucleotides.

HC/BTLP of the invention is structurally related to other proteins of the astacin protein family, by the results of sequencing the cDNA encoding hC/BTLP. The cDNA sequence of SEQ ID No:1 contains an open reading fme (nucleotide number 252 to 3293) encoding a polypeptide of 1013 amino acids of SEQ ID NO:2. The amino acid sequence of Table 2 (SEQ ID NO:2) has about 93.4% indentity (using BlastP) in 945 of 1012 amino acid residues with mus musculus (mouse) mammalian tolloid-like protein. GenBank Accession #U34042. The nucleotide sequence of Table 1 (SEQ ID NO: 1) has about 88.4% identity (using BlastN) in 2731 of 3089 nuclecoide residues with mus musculus mammalian tolloid-like protein. GenBank Accession #U34042. Thus, hC/BTLP polypeptides and polynucleotides of the present inventon are expect to have, inter alia, similar biological functions/properties to their homologous polypeptides and polynucleotides, and their uilit is obvious to anyone skilled in the art.

TABLE 1ᵃ

```
   1 CTTACCTGCC CTCCGCCCAC CCGTGGGCCC CTAGCCAACT TCTCCCTGCG
  51 ACTGGGGGTA ACAGGCAGTG CTTGCCCTCT CTACTGTCCC GGCGGCATCC
 101 ACATGTTTCC GGACACCTGA GCACCCCGGT CCCGCCGAGG AgCCTCCGGG
 151 TGGGGAGAAg AgCACCGGTG CCCCTAGCCC CGCACATCAg CGCGGACCGC
 201 GGCTGCCTAA CtTCTGGGTC CCGTCCCtTC CTTTTCCTCC GGGGGAgGAg
 251 GATGGGGTTG GGGACgCTTT CCCCGAgGAT GCTCGTGTGG CTGGTGGCCT
 301 CGGGGATTGT TTTCTACGGG GAgCTaTGGG TCTGCGCTGG CCTCgATTAT
 351 GATTACACTT TTGATGGGAA CgAAgAgGAT AAAACAGAGA CTATAGATTA
 401 CAAGGACCCG TGTAAAGCCG CTGTATTTTG GGGCGATATT GCCTTAGATG
 451 ATGAAGACTT AAATATCTTT CAaATAGATA GGACAATTGA CCTTACGCAG
 501 AACCCCTTTG GAAACCTTGG ACATACCACA GGTGGACTTG GAGACCATGC
 551 TATGTCAAAG AAGCGAGGGG CCCTCTACCA ACTTATAGAC AGGATAAGAA
 601 GAATTGGCTT TGGCTTGGAG CAAAACAACA CAGTTAAGGG AAAAGTACCT
 651 CTACAATTCT CAGGGCAAAA TGAGAAAAAT cGAGTTCCCA GAGCCGCTAC
 701 ATCAAGAACG GAAAGAgTAT GGCCTGGAGG CGTTATTCCT TATGTTATAG
 751 GAGGaAACTT CACTGGCAGC CAGAGAGCCA TGTTCAAGCA GGCCATGAGG
 801 CACTGGGaAA AGCACACATG TGTGACTTTC ATAGAAAGAA GTGATGAAGA
 851 GAGTTACATT GTATTCACCT ATAGGCCTTG TGGATGCTGC TCCTATGTAG
 901 GTcGGCGAGG AAgTGGACCT CAGGCAATCT CTATCGGCAA GAACTGTGAT
 951 AAATTTGGGA TtGTTGTTCA TGAATTGGGT CAtGTGATAG GCTTTTGGCA
1001 TGAACACACA AGACCAGATC GAGATAACCA CGTAACTATC ATAaGAGAAA
1051 ACATCCAGCC AGGTCAAgAG TACAATTTTC TGAAgATGGA GCCTGGAGAA
1101 GcAAACTCAC TTGGAGAAAG ATATGATTTC GACAGTATCA TGCACTATGC
1151 CAGGAACaCC TTCTCAAgGG GGATGTTTCt GGATACCATT CTCCCCTCCC
1201 GTGATGATAA TGGCAtACGT CCtGCAATTG GTCAGCgAAC CCGTCTAAGC
1251 aAAGGAgATA TCgCaCAGGC AAGAAAGCTG TATAGATGTC CAGCATGTGG
1301 AGAAACTcTA CAAGAATCCA ATGGCAACCT TTCCTCTCCA GGATTTCCCA
1351 ATGGCTACCC TTCTTACACA CACTGCATCT GGAGAGTTTC TGTGACCCCA
1401 GGGGAGAAGA TTGTTTTAAA TTTTACAACG ATGGATCTAT ACAAGAGTAG
1451 TTTGTGCTGG TATGACTATA TTGAAGTAAG AGACGGGTAC TGGAGAAAAT
1501 CACCTCTCCT TGgTAGATTC TGTGGGGACA AAtGCCTGA AGTTCTTACT
1551 TCTACAGACA GCAGAATGTG GATTGAGTTT CGTAGCAGCA GTAATTGGGT
1601 AGGAAAAGGC TTTGCAGCTG TCTATGAAGC GATCTGTGGA GGTGAGATAC
1651 GTAAAAATGA AGGACAGATT CAGTCTCCCA ATTATCCTGA TGACTATCGC
1701 CCGATGAAgG AATGTGTGTG GAAAATAACA GTGTCTGAGA GCTACCACGT
1751 CGGGCTGACC TTTCAGTCCT TTGAGATTGA AGACATGAC AATTGTGCTT
1801 ATGACTACCT GGAAGTTAGA GATGGAACCA GTGAAAATAG CCCTTTGATA
1851 GGGCGTTTCT GTGGTTATGA CAAACCTGAA GACATAAGAT CTACCTCCAA
1901 TACTTTGTGG ATGAAGTTTG TTTCTGACGG AACTGTGAAC AAAGCAGGGT
1951 TTGCTGCTAA CTTTTTTAAA GAGGAAGATG AGTGTGCCAA ACCTGACCGT
```

TABLE 1ᵃ-continued

```
2001 GGAGGCTGTG AGCAGCGATG TCTGAACACT CTGGGCAGTT ACCAGTGTGC
2051 CTGTGAGCCT GGCTATGAGC TGGGCCCAGA CAGAAGGAGC TGTGAAGCTG
2101 CTTGTGGTGG ACTTCTTACC AAACTTAACG GCACCATAAC CACCCCTGGC
2151 TGGCCCAAGG AGTACCCTCC TAATAAGAAC TGTGTGTGGC AAGTGGTTGC
2201 ACCAACCCAG TACAGAATTT CTGTGAAGTT TGAGTTTTTT GAATTGGAAG
2251 GCAATGAgGT TTGCAAATAT GATTATGTGG AGATCTGGAG TGGTCTTTCC
2301 TCTGAGTCTA AACTGCATGG CAAATTCTGT GGCGCTGAAG TGCCTGAAGT
2351 GATCACATCC CAGTTCAACA ATATGAGAAT TGAATTCAAA TCTGACAATA
2401 CTGTATCCAA GAAGGGCTTC AAAGCACATT TTTTCTCAGA CAAAGATGAA
2451 TGCTCTAAGG ATAATGGTGG ATGTCAGCAC GAATGTGTCA ACACGATGGG
2501 GAGCTACATG TGTCAATGCC GTAATGGATT TGTGCTACAT GACAATAAAC
2551 ATGATTGCAA GGAAGCTGAG TGTGAACAGA AGATCCACAG TCCAAGTGGC
2601 CTCATCACCA GTCCCAACTG GCCAGACAAG TACCCAAGCA GGAAAGAATG
2651 CACTTGGGAA ATCAGCGCCA CTCCTGGCCA CCGAATCAAA TTAGCCTTTA
2701 GTGAATTTGA GATTGAGCAG CATCaaGAAT GTGCTTATGA CCACTTAGAA
2751 GTATTTGATG GAGAAACAGA AAAGTCACCG ATTCTTGGAC GACTATGTGG
2801 CAACAAGATA CCAGATCCCC TTGTGGCTAC TGGAAATAAA ATGTTTGTTC
2851 GGTTTGTTTC TGATGCATCT GTTCAAAGAA AAGGCTTTCA AGCCACACAT
2901 TCTACAGAGT GTGGCGGACG ATTGAAAGCA GAATCAAAAC CAAGAGATCT
2951 GTACTCACAT GCTCAGTTTG GTGATAACAA CTACCCAGGA CAGGTTGACT
3001 GTGAATGGCT ATTAGTATCA GAACGGGGCT CTCGACTTGA ATTATCCTTC
3051 CAGACATTTG AAGTGGAGGA AGAAGCgGAC TGTGGCTATG ACTATGTGGA
3101 GCTCTTTGAT GGTCTTGATT CAACAGCTGT GGGGCTTGGT CGATTCTGTG
3151 GATCCGGGCC ACCAGAAGAG ATTTATTCAA TTGGAGATTC AGTTTTAATT
3201 CATTTCCACA CTGATGACAC AATCAACAAG AAGGGATTTC ATATAAGATA
3251 CAAAAGCATA AGATATCCAG ATACCACACA TACCAAAAAA TAACACCAAA
3301 ACCTCTGTCA GAACACAAAG GAATGTGCAT AATGGAGAGA AGACATATTT
3351 TTTTTAAAAC TGAAGATATT GGCACAAATG TTTTATACAA AGAGTTTGAA
3401 CAAAAAATCC CTGTAAGACC AGAATTATCT TTGTACTAAA AGAGAAGTTT
3451 CCAGCAAAAC CCTCATCAGC ATTACAAGGA TATTTGAACT CCATGCTTGA
3501 TGGTATTAAT AAAGCTGGTG AAAGGGCATC ATATACTTCA AGGAAGACTC
3551 TACAAGCTTT TGTTCACAGC TTGAAATAGA TGCCTCACAA TTCAGACAGT
3601 TTAATTCAGG AACTGTGACC CTGAAGTGTT CTTTTTGACA ATTTGTCAAG
3651 ATTTAGGGAC ATAAAATGAT CTTGCAGGTC GTAAACTGGA AACAGTATT
3701 TTGGTTGTCT TAGGATAATT GCTGACTTTG TATCTTGGAT ACAGTGTAAA
3751 CCAGATCCAT ATAAGGTGAA TGTGAAATGG GAGTCTTCTG AGGGTGATTT
3801 GTACTTTCCA TGTGTATGTG TGTGTCTGGT GTTTGGAAAC TGGGATATTT
3851 CAGCTTCATT ATTTCCACTT GCAGGCCAGC TTAACCTCTG AAACACAAAT
3901 GATCTTGAGA CCACTTTAGT GTACTTACAT TTAGATGAGT TTGAAATCTC
```

TABLE 1ᵃ-continued

```
3951 AATGGTGTCT AATTATTGCA GTTAAATTCT AGACATCAGT TCTTTAAGTC
4001 TCAGAAAACG CCCAGTGAAT TGGTAAACTT AGTTCTTTTT TTTGGAAGTG
4051 CTGCCTTTTC ACACCAAATC AAGAAGCCT GTGATGTCTT ATGAACCTTA
4101 TGAGAAAACT CCGAAGAGGT GTGAGCAGGA TTCTTCTGAA TGACTGTCTG
4151 GATGGTTCAT TACTCAAGTT ACTGCTGCTG CTATTGTCTT TCCTTTGTTG
4201 TCGATCTGTT ATTGTTGTAT TATTATTGTT GATGTTGTCA TGGTTAATCT
4251 ATTTTTTAAA ATTGAAATGA AGCAGAAGTA GGCCTTGTGA AACTGAAAG
4301 GTCTCTTTCA TTTTTCTCTT CCTGGGATTC ATTTTTTCAA AACACAATGC
4351 TGGAAAAAAA AGATTTGTTT CTGAAAGACT TCTTATGGTG CTATTCCATA
4401 AACTTTTTTT CAAACAAGTT TTTGACCTTT GAGCCAACCC ACCCGTAGAC
4451 TACGAATGTC TCCCTATGGC TGGTAGCATT TGAAGACTAA AGACTTGTCA
4501 AATATATCAA GAGTATATCA TTGCAAGGGC AGCACTTGTC CTGTGGAACA
4551 ACTACTTATA ATGCCTTAGA ATTCCTGCAC ATGATCAAAC AGATCCTCCT
4601 AAAACACACC TTTTGAAATG TTGAACATAA TAGTGTATGT TAATTAACAG
4651 CTCTATGAAG AAAATCCATT TCCATGACTG AAGCATTGGA TATAAATATG
4701 GTGTCCTGCT TTTTTTGTAG AAAATGTAAT TTGAGGATGA ATTTTCTGCT
4751 TTAAAGGCAT GTGTGTTTTT AAAATTAATG AATGTAGATG TGTGATTGTC
4801 TGAGTGAGTG AAACTACAAG AGGTAAAAAA TAATGGGTGG TTGAAAAGTT
4851 AAAATGTATG TGCCAAGTTC TACTAGAATT CCATTTGAAA TAGCACCTTC
4901 CTTAGGTTTC ATGGACAAAT AATGGGAACT TCTAATTTTG ATCAATCCCA
4951 TTAAAAAAAG GCTCTTTCCT TTAGAGAAAC TCTATTTTGA TGTCAATATA
5001 GATTACTGTA TGAAGTAGCT TTGTGTCTGT TACCTGTCCA TGAGCATACA
5001 ACATTGAATA CAATTGGGTG TATTCTTTCA GTTTTACACA ATTAAAGTAT
5101 ACACACAGAT GTAAAAAAAA AAAAAAAAA AAAAAAAAC TCGAG
```

ᵃA nucleotide sequence of a hC/BTLP (SEQ ID NO:1).

TABLE 2ᵇ

```
  1 MGLGTLSPRM LVWLVASGIV FYGELWVCAG LDYDYTFDGN EEDKTETIDY
 51 KDPCKAAVFW GDIALDDEDL NIFQIDRTID LTQNPFGNLG HTTGGLGDHA
101 MSKKRGALYQ LIDRIRRIGF GLEQNNTVKG KVPLQFSGQN EKNRVPRAAT
151 SRTERVWPGG VIFYVIGGNF TGSQRAMFKQ AMRHWEKHTC VTFIERSDEE
201 SYIVFTYRPC GCCSYVGRRG SGPQAISIGK NCDKFGIVVH ELGHVIGFWH
251 EHTRPDRDNH VTIIRENIQP GQEYNFLKME PGEANSLGER YDFDSIMHYA
301 RNTFSRGMFL DTILPSRDDN GIRPAIGQRT RLSKGDIAQA RKLYRCPACG
351 ETLQESNGNL SSPGFFNGYP SYTHCIWRVS VTPGEKIVLN FTTMDLYKSS
401 LCWYDYIEVR DGYWRKSPLL GRFCGDKLPE VLTSTDSRMW IEFRSSSNWV
451 GKGFAAVYEA ICGGEIRKNE GQIQSPNYPD DYRPMKECVW KITVSESYHV
501 GLTFQSFEIE RHDNCAYDYL EVRDGTSENS PLIGRFCGYD KPEDIRSTSN
551 TLWMKFVSDG TVNKAGFAAN FFKEEDECAK PDRGGCEQRC LNTLGSYQCA
601 CEPGYELGPD RRSCEAACGG LLTKLNGTIT TPGWPKEYPP NKNCVWQVVA
```

TABLE 2[b]-continued

```
651 PTQYRISVKF EFFELEGNEV CKYDYVEIWS GLSSESKLHG KFCGAEVPEV

701 ITSQFNNMRI EFKSDNTVSK KGFKAHFFSD KDECSKDNGG CQHECVNTMG

751 SYMCQCRNGF VLHDNKHDCK EAECEQKIHS PSGLITSPNW PDKYPSRKEC

801 TWEISATPGH RIKLAFSEFE IEQHQECAYD HLEVFDGETE KSPILGRLCG

851 NKIPDPLVAT GNKMFVRFVS DASVQRKGFQ ATHSTECGGR LKAESKPRDL

901 YSHAQFGDNN YPGQVDCEWL LVSERGSRLE LSFQTFEVEE EADCGYDYVE

951 LFDGLDSTAV GLGRFCGSGP PEEIYSIGDS VLIHFHTDDT INKKGFHIRY

1001 KSIRYPDTTH TKK
```

[b]An amino acid sequence of a hC/BTLP (SEQ ID NO: 2)

One polynucleotide of the present invention encoding hC/BTLP may be obtained using standard cloning and screening, from a cDNA library derived from mRNA in cells of human 8 week old human embryo using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polvnucleotides of the invention can also be obtained from natural sources such as genomic DNA libraries or can be synthesized using well known and commercially available techniques.

The nucleotide sequence encoding hC/BTLP polypeptide of SEQ ID NO:2 may be identical to the polypeptide encoding sequence contained in Table 1 (nucleotide number 252 to 3293 of SEQ ID NO: 1), or it may be a sequence, which as a result of the redundancy (degeneracy) of the genetic code, also encodes the polypeptide of SEQ ID NO:2.

When the polynucleotides of the invention are used for the recombinant production of hC/BTLP polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which filitates purification of the fused polypeptide can be encoded. In certain preferred embodiments of this aspect of the invention, the marker sequence is a hexa-histidine peptide, as provided in the pQE vector (Qiagen, Inc.) and described in Gentz etal., *Proc Natl Acad Sci USA* (1989) 86:821–824, or is an HA tag. The polynucleotide may also contain non-coding 5' and 3' sequences, such as transcribed, non-translated sequences, splicing and polvadenylation signals, ribosome binding sites and sequences that stabilize mRNA.

Further preferred embodiments are polynucleotides encoding hC/BTLP variants comprising the amino acid sequence of hC/BTLP polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO: 3) encoding the amino acid sequence of Table 4 (SEQ ID NO: 4).

TABLE 3[c]

```
GAATTCGGCA CGAGCTCGTG CCGCTCGTGC CGCGGGTACT GGAGAAAATC      60
ACCTCTCCTT

GATTCTGTGG GGACAAATTG CCTGAAGTTC TTACTTCTAC AGACAGCAGA ATGTG- 120
GATTG

AGTTTCGTAG CAGCAGTAAT TGGGTAGGAA AAGGCTTTGC AGCTGTCTAT GAAGC- 180
GATCT

GTGGAGGTGA GATACGTAAA AATGAAGGAC AGATTCAGTC TCCCAATTAT CCT-   240
GATGACT

ATCGCCCGAT GAAAGAATGT GTGTGGAAAA TAACAGTGTC TGAGAGCTAC        300
CACGTCGGGC

TGACCTTTCA GTCCTTTGAG ATTGAAAGAC ATGACAATTG TGCTTATGAC TAC-   360
CTGGAAG

TTAGAGATGG AACCAGTGAA AATAGCCCTT TGATAGGGCG TTTCTGTGGT TATGA- 420
CAAAC

CTGAAGACAT AAGATCTACC TCCAATACTT TGTGGATGAA GTTTGTTTCT GACG-  480
GAACTG

TGAACAAAGC AGGGTTTGCT GCTAACTTTT TTAAAGAGGA AGATGAGTGT         540
GCCAAACCTG

ACCGTGGAGG CTGTGAGCAG CGATGTCTGA ACACTCTGGG CAGTTACCAG TGTGC- 600
CTGTG
```

TABLE 3<sup>c</sup>-continued

```
AGCCTGGCTA TGAGCTGGGC CCAGACAGAA GGAGCTGTGA AGCTGCTTGT GGTG-     660
GACTTC

TTACCAAACT TAACGGCACC ATAACCACCC CTGGCTGGCC CAAGGAGTAC CCTC-     720
CTAATA

AGAACTGTGT GTGGCAAGTG GTTGCACCAA CCCAGTACAG AATTTCTGTG           780
AAGTTTGAGT

TTTTTGAATT GGAAGGCAAT GAAGTTTGCA AATATGATTA TGTGGAGATC           840
TGGAGTGGTC

TTTCCTCTGA GTCTAAACTG CATGGCAAAT TCTGTGGCGC TGAAGTGCCT GAAGT-    900
GATCA

CATCCCAGTT CAACAATATG AGAATTGAAT TCAAATCTGA CAATACTGTA TCCAA-    960
GAAGG

GCTTCAAAGC ACATTTTTC TCAGACAAAG ATGAATGCTC TAAGGATAAT GGTG-     1020
GATGTC

AGCACGAATG TGTCAACACG ATGGGGAGCT ACATGTGTCA ATGCCGTAAT          1080
GGATTTGTGC

TACATGACAA TAAACATGAT TGCAAGGAAG CTGAGTGTGA ACAGAAGATC          1140
CACAGTCCAA

GTGGCCTCAT CACCAGTCCC AACTGGCCAG ACAAGTACCC AAGCAGGAAA GAATG-   1200
CACTT

GGGAAATCAG CGCCACTCCT GGCCACCGAA TCAAATTAGC CTTTAGTGAA          1260
TTTGAGATTG

AGCAGCATCG GGAATGTGCT TATGACCACT TAGAAGTATT TGATGGAGAA ACA-     1320
GAAAAGT

CACCGATTCT TGGACGACTA TGTGGCAACA AGATACCAGA TCCCCTTGTG          1380
GCTACTGGAA

ATAAAATGTT TGTTCGGTTT GTTTCTGATG CATCTGTTCA AGAAAAGGC           1440
TTTCAAGCCA

CACATTCTAC AGAGTGTGGC GGACGATTGA AAGCAGAATC AAAACCAAGA GATCT-   1500
GTACT

CACATGCTCA GTTTGGTGAT AACAACTACC CAGGACAGGT TGACTGTGAA TGGC-    1560
TATTAG

TATCAGAACG GGGCTCTCGA CTTGAATTAT CCTTCCAGAC ATTTGAAGTG GAG-     1620
GAAGAAG

CAGACTGTGG CTATGACTAT GTGGAGCTCT TTGATGGTCT TGATTCAACA GCT-     1680
GTGGGGC

TTGGTCGATT CTGTGGATCC GGGCCACCAG AAGAGATTTA TTCAATTGGA GAT-     1740
TCAGTTT

TAATTCATTT CCACACTGAT GACACAATCA ACAAGAAGGG ATTTCATATA AGATA-   1800
CAAAA

GCATAAGATA TCCAGATACC ACACATACCA AAAAATAACA CCAAAACCTC TGTCA-   1860
GAACA

CAAAGGAATG TGCATAATGG AGAGAAGACA TATTTTTTTT AAAACTGAAG ATAT-    1920
TGGCAC

AAATGTTTTA TACAAAGAGT TTGAACAAAA AATCCCTGTA AGACCAGAAT          1980
TATCTTTGTA

CTAAAAGAGA AGTTTCCAGC AAAACCCTCA TCAGCATTAC AAGGATATTT          2040
GAACTCCATG

CTTGATGGTA TTAATAAAGC TGGTGAAAGG GCATCATATA CTTCAAGGAA GACTC-   2100
TACAA

GCTTTTGTTC ACAGCTTGAA ATAGATGCCT CACAATTCAG ACAGTTTAAT TCAG-    2160
GAACTG

TGACCCTGAA GTGTTCTTTT TGACAATTTG TCAAGATTTA GGGACATAAA          2220
ATGATCTTGC
```

TABLE 3[c]-continued

```
AGGTCGTAAA CTGGAAAACA GTATTTTGGT TGTCTTAGGA AATTGCTGA CTTTG-   2280
TATCT

TGGATACAGT GTAAACCAGA TCCATATAAG GTGAATGTGA AATGGGAGTC TTCT-   2340
GAGGGT

GATTTGTACT TTCCATGTGT ATGTGTGTGT CTGGTGTTTG GAAACTGGGA         2400
TATTTCAGCT

TCATTATTTC CACTTGCAGG CCAGCTTAAC CTCTGAAACA CAAATGATCT         2460
TGAGACCACT

TTAGTGTACT TACATTTAGA TGAGTTTGAA ATCTCAATGG TGTCTAATTA TTG-    2520
CAGTTAA

ATTCTAGACA TCAGTTCTTT AAGTCTCAGA AAACGCCCAG TGAATTGGTA AACT-   2580
TAGTTC

TTTTTTTTGG AAGTGCTGCC TTTTCACACC AAATCCAAGA AGCCTGTGAT GTCT-   2640
TATGAA

CCTTATGAGA AAACTCCGAA GAGGTGTGAG CAGGATTCTT CTGAATGACT GTCTG-  2700
GATGG

TTCATTACTC AAGTTACTGC TGCTGCTATT GTCTTTCCTT TGTTGTCGAT CTGT-   2760
TATTGT

TGTATTATTA TTGTTGATGT TGTCATGGTT AATCTATTTT TTAAAATTGA AAT-    2820
GAAGCAG

AAGTAGGCCT TGTGAGAACT GAAAGGTCTC TTTCATTTTT CTCTTCCTGG GAT-    2880
TCATTTT

TTCAAAACAC AATGCTGGAA AAAAAAGATT TGTTTCTGAA AGACTTCTTA TGGT-   2940
GCTATT

CCATAAACTT TTTTTCAAAC AAGTTTTTGA CCTTTGAGCC AACCCACCCG TAGAC-  3000
TACGA

ATGTCTCCCT ATGGCTGGTA GCATTTGAAG ACTAAAGACT TGTCAAATAT ATCAA-  3060
GAGTA

TATCATTGCA AGGGCAGCAC TTGTCCTGTG GAACAACTAC TTATAATGCC TTA-    3120
GAATTCC

TGCACATGAT CAAACAGATC CTCCTAAAAC ACACCTTTTG AAATGTTGAA CAT-    3180
AATAGTG

TATGTTAATT AACAGCTCTA TGAAGAAAAT CCATTTCCAT GACTGAAGCA TTG-    3240
GATATAA

ATATGGTGTC CTGCTTTTTT TGTAGAAAAT GTAATTTGAG GATGAATTTT         3300
CTGCTTTAAA

GGCATGTGTG TTTTTAAAAT TAATGAATGT AGATGTGTGA TTGTCTGAGT GAGT-   3360
GAAACT

ACAAGAGGTA AAAAATAATG GGTGGTTGAA AAGTTAAAAT GTATGTGCCA AGTTC-  3420
TACTA

GAATTCCATT TGAAATAGCA CCTTCCTTAG GTTTCATGGA CAAATAATGG GAACT-  3480
TCTAA

TTTTGATCAA TCCCATTAAA AAAAGGCTCT TTCCTTTAGA GAAACTCTAT         3540
TTTGATGTCA

ATATAGATTA CTGTATGAAG TAGCTTTGTG TCTGTTACCT GTCCATGAGC ATA-    3600
CAACATT

GAATACAATT GGGTGTATTC TTTCAGTTTT ACACAATTAA AGTATACACA CAGAT-  3660
GTAAA

AAAAAAAAAA AAAAAAAAA AAAACTCGAG                                3690
```

[c]A partial nucleotide sequence of a hC BTLP (SEQ ID NO: 3).

TABLE 4[d]

```
Phe Cys Gly Asp Lys Leu Pro Glu Val Leu Thr Ser Thr Asp Ser Arg
 1               5                      10                  15

Met Trp Ile Glu Phe Arg Ser Ser Asn Trp Val Gly Lys Gly Phe
            20                  25                  30

Ala Ala Val Tyr Glu Ala Ile Cys Gly Gly Glu Ile Arg Lys Asn Glu
            35              40                  45

Gly Gln Ile Gln Ser Pro Asn Tyr Pro Asp Asp Tyr Arg Pro Met Lys
    50                  55                  60

Glu Cys Val Trp Lys Ile Thr Val Ser Glu Ser Tyr His Val Gly Leu
65              70                  75                      80

Thr Phe Gln Ser Phe Glu Ile Glu Arg His Asp Asn Cys Ala Tyr Asp
                85                  90                  95

Tyr Leu Glu Val Arg Asp Gly Thr Ser Glu Asn Ser Pro Leu Ile Gly
            100                 105                 110

Arg Phe Cys Gly Tyr Asp Lys Pro Glu Asp Ile Arg Ser Thr Ser Asn
            115                 120                 125

Thr Leu Trp Met Lys Phe Val Ser Asp Gly Thr Val Asn Lys Ala Gly
    130                 135                 140

Phe Ala Ala Asn Phe Phe Lys Glu Glu Asp Glu Cys Ala Lys Pro Asp
145                 150                 155                 160

Arg Gly Gly Cys Glu Gln Arg Cys Leu Asn Thr Leu Gly Ser Tyr Gln
                165                 170                 175

Cys Ala Cys Glu Pro Gly Tyr Glu Leu Gly Pro Asp Arg Arg Ser Cys
            180                 185                 190

Glu Ala Ala Cys Gly Gly Leu Leu Thr Lys Leu Asn Gly Thr Ile Thr
            195                 200                 205

Thr Pro Gly Trp Pro Lys Glu Tyr Pro Pro Asn Lys Asn Cys Val Trp
    210                 215                 220

Gln Val Val Ala Pro Thr Gln Tyr Arg Ile Ser Val Lys Phe Glu Phe
225                 230                 235                 240

Phe Glu Leu Glu Gly Asn Glu Val Cys Lys Tyr Asp Tyr Val Glu Ile
                245                 250                 255

Trp Ser Gly Leu Ser Ser Glu Ser Lys Leu His Gly Lys Phe Cys Gly
            260                 265                 270

Ala Glu Val Pro Glu Val Ile Thr Ser Gln Phe Asn Asn Met Arg Ile
            275                 280                 285

Glu Phe Lys Ser Asp Asn Thr Val Ser Lys Gly Phe Lys Ala His
    290                 295                 300

Phe Phe Ser Asp Lys Asp Glu Cys Ser Lys Asp Asn Gly Gly Cys Gln
305                 310                 315                 320

His Glu Cys Val Asn Thr Met Gly Ser Tyr Met Cys Gln Cys Arg Asn
                325                 330                 335

Gly Phe Val Leu His Asp Asn Lys His Asp Cys Lys Glu Ala Glu Cys
            340                 345                 350

Glu Gln Lys Ile His Ser Pro Ser Gly Leu Ile Thr Ser Pro Asn Trp
            355                 360                 365

Pro Asp Lys Tyr Pro Ser Arg Lys Glu Cys Thr Trp Glu Ile Ser Ala
    370                 375                 380

Thr Pro Gly His Arg Ile Lys Leu Ala Phe Ser Glu Phe Glu Ile Glu
385                 390                 395                 400

Gln His Arg Glu Cys Ala Tyr Asp His Leu Glu Val Phe Asp Gly Glu
                405                 410                 415

Thr Glu Lys Ser Pro Ile Leu Gly Arg Leu Cys Gly Asn Lys Ile Pro
```

TABLE 4[d]-continued

|     |     |     |     |     |     | 420 |     |     |     |     | 425 |     |     |     |     | 430 |     |     |     |
| --- | --- | --- | --- | --- | --- | --- | --- | --- | --- | --- | --- | --- | --- | --- | --- | --- | --- | --- | --- |
| Asp | Pro | Leu 435 | Val | Ala | Thr | Gly | Asn 440 | Lys | Met | Phe | Val | Arg 445 | Phe | Val | Ser |
| Asp | Ala 450 | Ser | Val | Gln | Arg | Lys 455 | Gly | Phe | Gln | Ala | Thr 460 | His | Ser | Thr | Glu |
| Cys 465 | Gly | Gly | Arg | Leu | Lys 470 | Ala | Glu | Ser | Lys | Pro 475 | Arg | Asp | Leu | Tyr | Ser 480 |
| His | Ala | Gln | Phe | Gly 485 | Asp | Asn | Asn | Tyr | Pro 490 | Gly | Gln | Val | Asp | Cys 495 | Glu |
| Trp | Leu | Leu | Val | Ser 500 | Glu | Arg | Gly | Ser 505 | Arg | Leu | Glu | Leu | Ser 510 | Phe | Gln |
| Thr | Phe | Glu 515 | Val | Glu | Glu | Glu | Ala 520 | Asp | Cys | Gly | Tyr | Asp 525 | Tyr | Val | Glu |
| Leu | Phe | Asp 530 | Gly | Leu | Asp | Ser 535 | Thr | Ala | Val | Gly | Leu 540 | Gly | Arg | Phe | Cys |
| Gly | Ser | Gly | Pro | Pro | Glu 550 | Glu | Ile | Tyr | Ser | Ile 555 | Gly | Asp | Ser | Val | Leu 560 |
| 545 | | | | | | | | | | | | | | | |
| Ile | His | Phe | His | Thr 565 | Asp | Asp | Thr | Ile | Asn 570 | Lys | Lys | Gly | Phe | His 575 | Ile |
| Arg | Tyr | Lys | Ser 580 | Ile | Arg | Tyr | Pro | Asp | Thr 585 | Thr | His | Thr | Lys 590 | Lys |

[d]A partial amino acid sequence of a hC BTLP (SEQ ID NO: 4).

The present invention further relates to polvnucleotides that hybridize to the herein above-described sequences. In this regard, the present invention especially relates to polynucleotides which hybridize under stringent conditions to the herein above-described polynucleotides. As herein used, the term "stringent conditions" means hvbridization will occur only if there is at least 80%, and preferably at least 90%, and more preferably at least 95%, vet even more preferably 97–99% identity between the sequences.

Polynucleotides of the invention, wvhich are identical or sufficiently identical to a nucleotide sequence contained in SEQ ID NO: 1 or a fragment thereof (including that of SEQ ID NO:3), may be used as hybridization probes for cDNA and genomic DNA, to isolate full-length cDNAs and genomic clones encoding hC/BTLP polypeptide and to isolate cDNA and genomic clones of other genes (including genes encoding homologs and orthologs from species other than human) taat have a high sequence similarity to the hC/BTLP gene. Such hybridization techniques are known to those of skill in the art. Typically these nucleotide sequences are 80% identical, preferably 90% identical, more preferably 95% identical to that of the rerent. The probes generally will comprise at least 15 nucleotides. Preferably, such probes will have at least 30 nucleotides and may have at least 50 nucleotides. Particularly preferred probes will range betnveen 30 and 50 nucleotides.

In one embodiment, to obtain a polynucleotide encoding hC/BTLP polypeptide, including homologs and orthologs from species other than human, comprises the steps of screening an appropriate library under stingent hybridization conditions with a labeled probe having the SEQ ID NO: 1 or a fragment thereof (including that of SEQ ID NO: 3), and isolating full-length cDNA and genomic clones containing said polynucleotide sequence. Such hybridiztion techniques are well known to those of skill in the art. Thus in another aspect, hC/BTLP polynucleotides of the present invention further include a nucleotide sequence comprising a nucleotide sequence that hybridize under stringent condition to a nucleotide sequence having SEQ ID NO: 1 or a fragwent thereof (including that of SEQ ID NO:3). Also included with hC/BTLP polypeptides are pol peptide comprising amino acid sequence encoded by nucleotide sequence obtained by the above hybridization condition. Stringent hybridization conditions are as defined above or, alternatively, conditions under overnight incubation at 42° C. in a solution comprising: 50% formamide, 5×SSC (150mM NaCl, 15mM trisodium citrate), 50 mM sodium phosphate (pH7.6), 5×Denhardt's solution, 10% dextran sulfate, and 20 microgramrnil denatured, sheared salmon sperm DNA, followed by washing the filters in 0×SSC at about 65° C.

The polynucleotides and polymeptides of the present invention may be employed as research reagents and materials for discovery of treatments and diagnostics to animal and human disease.

Vectors, Host Cells, Expression

The present invention also relates to vectors which comprise a polynucleotde or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polvnucleotides of the present invention. Introduction of polynucleotides into host cells can be effected by methods described in many standard laboratory manuals, such as Davis et al, BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate trnsfection DEAE-dextran mediated tfansection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fingal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression svstems can be used. Such systems include, among others, chromosomal, episomal and virus-derived svstns, e.g., vectors derived from bacterial plasmids, from bacteriophage, from transposons, from veast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the hC/BTLP polypeptide is to be expressed for use in screening assays, generally, it is preferred that the polypeptide be produced at the surface of the cell. In this event, the cells may be harvested prior to use in the screening assay. If hC/BTLP polypeptide is secreted into the medium, the medium can be recovered in order to recover and purify the polypeptide; if produced intracellularly, the cells must first be lysed before the polypeptide is recovered. hC/BTLP polypeptides can be recovered and purified from recombinant cell cultures by well-known methods including armoniun sum late or ethanol precipitation, acid extraction, anion or cation exchange chromatography, phosphocellulose chromatography, hydrophobic interaction chromatography, affinit chromatography, hydroxylapatite chromatophy and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of hC/BTLP polynucleotides for use as diagnostic reagents. Detection of a mutated form of hC/BTLP gene associated with a dysfunction will provide a diagnostic tool that can add to or define a diagnosis of a disease or susceptibility to a disease which results from under-expression, overexpression or altered expression of hC/BTLP. Individuals carrying mutations in the hC/BTLP gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the nomwal genotype. Point mutations can be identified by hybridizing amplified DNA to labeled hC/BTLP nucleotide sequences. Perfctly matched sequences can be distinguished from mismatched duplexes by RNase digestion or by differences in melting temperatures. DNA sequence differences may also be detected by alterations in electrophoretic mobility of DNA fragments in gels, with or without denug agents, or by direct DNA sequencing. See, e.g., Myers etal., *Science* (1985)230:1242. Sequence changes at specific locations mayalso be revealed by nuclease protection assays, such as RNase and S1 protection or the chemical cleavage method. See Cotton et al., *Proc Natl Acad Sci USA* (1985) 85: 4397–4401. In another embodiment, an array of oligonucleotides probes comprising hC/BTLP nucleotide sequence or fiagents thereof can be constructed to conduct efficient screening of e.g., genetic mutations. Array technology methods are well known and have general applicabilitv and can be used to address a variety of questions in molecular genetics including gene expression, genetic linkage, and genetic variability. (See for example: M.Chee et al., *Science*, Vol 274, pp 610–613 (1996)).

The diagnostic assays offer a process for diagnosing or deternining a susceptibility to restenosis, atherosclerosis, congestive heart failure (CHF), chronic obstructive pulmonary disease (COPD), benign prostatic hypertrophy (BPH), nephritis, fibrosis, glomerulonephritis, gliosis, cirrhosis and anomalies of wound healing, such as keloidsthrough detection of mutation in the hC/BTLP gene by the methods described.

In addition, restenosis, atherosclerosis, congestive heart failure (CHF), chronic obstructive pulmonary disease (COPD), benign prostatic hnpetrophy (BPH), nephritis, fibrosis, glomerulonephritis, gliosis, cirrhosis and anomalies of wound healing, such as keloids, can be diagnosed by methods comprising determining from a sample derived from a subject an abnormally decreased or increased level of hC/BTLP polypeptide or hC/BTLP mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an hC/BTLP polypeptide, in a sample derived from a host are well-known to those of skill in the art. Such assay methods include radioimmunoassays, competitive-binding assays, Western Blot analysis and ELISA assavs.

Thus in another aspect, the present invention relates to a diagonostic kit for a disease or suspectability to a disease, particularly restenosis, atherosclerosis, congestive heart failure (CHF), chronic obstructive pulmonary disease (COPD), benign prostatic hypertrophy (BPH), nephritis, fibrosis, glomerulonephritis, gliosis, cirrhosis and anomalies of wound healing, such as keloids, which comprises:

(a) a hC/BTLP polynucleotide, preferably the nucleotide sequence of SEQ ID NO: 1, or a fragment thereof, (b) a nucleotide sequence complementary to that of (a);

(c) a hC/BTLP polypeptide, preferably the polypeptide of SEQ ID NO: 2, or a fgment thereof; or (d) an antibody to a hC/BTLP polypeptide, preferably to the polypeptide of SEQ ID NO: 2. It will be appreciated that in any such kit, (a), (b), (c) or (d) may comprise a substantial component.

Chromosome Assays

The nucleotide sequences of the present invention are also valuable for chromosome identification. The sequence is specifically tailed to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the hC/BTLP polypeptides.

The term "immunospecific" means that the antibodies have substantial greater affinity for the polypeptides of the invention than their affinity for other related polypeptides in the prior art.

Antibodies generated against the hC/BTLP polypeptides can be obtained by administering the polypeptides or epitope-bearing fragments, analogs or cells to an anirral, preferably a nonhuman, using routine protocols. For preparation of monoclonal antibodies, any technique which provides antibodies produced by continuous cell line cultures can be used. Examples include the hybridoma technique (Kohler, G. and Milstein, C, *Nature* (1975)256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R Liss, Inc., 1985).

Techniques for the production of single chain antibodies (U.S. Pat. No. 4,946,778) can also be adapted to produce single chain antibodies to polypeptides of this invention. Also, trarsngenic mice, or other organisms including other mannials, may be used to express humanized antibodies.

The above-described antibodies may be employed to isolate or to identify clones expressing the polypeptide or to purify the polypeptides by affinity chromatography.

Antibodies against hC/BTLP polypeptides may also be employed to treat restenosis, atherosclerosis, congestive heart failure (CHF), chronic obstructive pulmonary disease (COPD), benign prostatic hypertrophy (BPH), nephritis, fibrosis, glomerulonephiitis, gliosis, cirrhosis and anomalies of wound healing, such as keloids, among others.

Vaccines

Another aspect of the invention relates to a method for inducing an immunological response in a mammal which comprises inoculating the mammal with hC/BTLP polypeptide, or a fragment thereof, adequate to produce antibody and/or T cell immune response to protect said animal from restenosis, atherosclerosis, congestive heart failure (CHF), chronic obstructive pulmonary disease (COPD), benign prostatic hypertrophy (BPH), nephritis, fibrosis, glomerulonephritis, gliosis, cirrhosis and anomalies of wound healing, such as keloids, among others. Yet another aspect of the invention relates to a method of inducing immunological response in a mammal which comprises, delivering hC/BTLP polypeptide via a vector directing expression of hC/BTLP polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a hC/BTLP polypeptide wherein the composition comprises a hC/BTLP polypeptide or hC/BTLP gene. The vaccine formulation may further comprise a suitable carrier. Since hC/BTLP polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The hC/BTLP polypeptide of the present invention may be employed in a screening process for compounds which activate (agonists) or inhibit activation of (antagonists, or otherwise called inhibitors) the hC/BTLP polypeptide of the present invention. Thus, polypeptides of the invention may also be used to assess identify agonist or antagonists from, fbr example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan et al., *Current Protocols in Immunology* 1(2):Chapter 5 (1991).

HC/BTLP polypeptides are responsible for many biological functions, including many pathologies. Accordingly, it is desirous to find compounds and drugs which stimulate hC/BTLP polypeptide on the one hand and which can inhibit the function of hC/BTLP polypeptide on the other hand. In general, agonists are employed for therapeutic and prophylactic purposes for such conditions as restenosis, atherosclerosis, congestive heart filure (CHF), chronic obstructive pulmonary disease (COPD), benign prostatic hypertrophy (BPH), nephritis, fibrosis, glomerulonephritis, gliosis, cirrhosis and anomalies of wound healing, such as keloids. Antagonists may be employed for a variety of therapeutic and prophylactic purposes for such conditions as restenosis, atherosclerosis, congestive heart failure (CHF), chronic obstructive pulmonary disease (COPD), benign prostatic hypertrophy (BPH), nephritis, fibrosis, glomerulonephritis, gliosis, cirrhosis and anomalies of wound healing, such as keloids In general, such screening procedures may involve using appropriate cells which express the hC/BTLP polypeptide or respond to hC/BTLP polypeptide of the present invention. Such cells include cells from mammals, yeast, Drosophila or E coli. Cells which express the hC/BTIP polypeptide (or cell membrane containing the expressed polypeptide) or respond to hC/BTLP polypeptide are then contacted with a test compound to observe binding, or stimulation or inhibition of a functional response. The ability of the cells which were contacted with the candidate compounds is compared with the same cells which were not contacted for hC/BTLP activity.

The assays may simply test binding of a candidate compound wherein adherence to the cells bearing the hC/BTLP polypeptide is detected by means of a label directly or indirectly associated with the candidate compound or in an assay involving competition with a labeled competitor. Further, these assays may test whether the candidate compound results in a signal generated by activation of the hC/BTLP polypeptide, using detection systems appropriate to the cells bearing the hC/BTLP polypeptide. Inhibitors of activation are generally assayed in the presence of a known agonist and the effect on activation by the agonist by the presence of the candidate compound is observed.

Further, the assays may simplv comprise the steps of mixing a candidate compound with a solution containing a hC/BTLP polypeptide to form a mixture, measuring hC/BTLP activity in the mixture, and comparing the hC/BTLP activity of the mixture to a standard.

The hC/BTLP cDNA, protein and antibodies to the protein may also be used to configure assays for detecting the effect of added compounds on the production of hC/BTLP mRNA and protein in cells. For example, an ELISA may be constructed for measuring secreted or cell associated levels of hC/BTLP protein using monoclonal and polyclonal antibodies by standard methods known in the art, and this can be used to discover agents which may inhibit or enhance the production of hC/BTLP (also called antagonist or agonist, respectively) from suitably manipulated cells or tissues.

The hC/BTLP protein may be used to identify membrane bound or soluble receptors, if any, through standard receptor binding techniques known in the art. These include, but are not limited to, ligand binding and crosslinking assays in which the hC/BTLP is labeled with a radioactive isotope (eg 125I), chemically modified (eg biotinylated), or fused to a peptide sequence suitable for detection or purification. and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of hC/BTLP wvhich compete with the binding of hC/BTLP to its receptors, if any. Standard methods for conducting screening assays are well understood in the art.

Examples of potential hC/BTLP polypeptide antagonists include antibodies or, in some cases, oligonucleotides or proteins wlich are closely related to the ligands, substrates, enzymes, receptors, etc., as the case may be, of the hC/BTLP polypeptide. e.g., a fragment of the ligands, substraes, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for hC/BTLP polypeptides; or compounds which decrease or enhance the production of hC/BTLP polypeptides, which comprises:

(a) a hC/BTLP polypeptide, preferably that of SEQ ID NO:2;

(b) a recombinant cell expressing a hC/BTLP polypeptide, preferably that of SEQ ID NO:2;

(c) a cell membrane expressing a hC/BTLP polkpeptide; preferably that of SEQ ID NO: 2; or (d) antibody to a hC/BTLP polypeptide, preferably that of SEQ ID NO: 2. It will be appreciated that in any such kit, (a), (b), (c) or (d) may comprise a substantial component.

Prophylactic and Therapeutic Methods

This invention provides methods of treating abnormal conditions such as, restenosis, atherosclerosis, congestive heart filure (CHF), chronic obstructive pulmonary disease (COPD), benign prostatic hypertrophy (BPH), nephritis, fibrosis, glomerulonephritis, gliosis, cirrhosis and anomalies of wound healing, such as keloids, related to both an excess of and insufficient amounts of hC/BTLP polypeptide activity.

If the activity of hC/BTLP polypeptide is in excess, several approaches are available. One approach comprises administering to a subject an inhibitor compound (antagonist) as hereinabove described along with a pharmacutically acceptable carrier in an amount effective to inhibit the function of the hC/BTLP polypeptide, such as, for example by blocking the binding of ligands, substrates, enzymes, receptors, etc., or by inhibiting a second signal, and thereby alleviating the abnormal condition. In another approach, soluble forms of hC/BTLP polypeptides still capable of binding the ligand, substrate, enzymes, receptors, etc. in competition with endogenous hC/BTLP polypeptide may be administered. Typical embodiments of such competitors comprise fragments of the hC/BTLP polypeptide.

In another approach, soluble forms of hC/BTLP polypeptides still capable of binding the ligand in competition with endogenous hC/BTLP polypeptide may be administered. Typical embodiments of such competitors comprise fragments of the hC/BTLP polypeptide.

In still another approach, expression of the gene encoding endogenous hC/BTLP polypeptide can be inhibited using expression blocking techniques. Known such techniques involve the use of antisense sequences, either internally generated or separately adrinistered. See, for example, O'Connor, *J Neurochem* (1991) 56:560 in *Olizodeoxvnucleotides as Antisense Inhibitors of Gene Expression*, CRC Press, Boca Raton, Fla. (1988). Alternatively, oligonucleotides which form triple helices with the gene can be supplied. See, for example, Lee et al, *Nucleic Acids Res* (1979) 6:3073; Cooney et al., *Science* (1988) 241:456; Dervan et al., Science (1991) 251:1360. These oligomers can be administered per se or the relevant oligomers can be expressed in vivo.

For treating abnormal conditions related to an underxpression of hC/BTLP and its activity, several approaches are also available. One approach comprises administering to a subject a therapeutically effective amount of a compound vhich activates hC/BTLP polypeptide, i.e., an agonist as described above, in combination with a phalrmaceutically acceptable carrier, to thereby alleviate the abnormal condition. Alternatively, gene therapy may be employed to effect the endogenous production of hC/BTLP by the relevant cells in the subject. For example, a polynucleotide of the invention may be engineered for expression in a replication defctive retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be admired to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of hC/BTLP polypeptides in combination with a suitable phamiaceutical carrier.

Formulation and Administration

Peptides, such as the soluble form of hC/BTLP polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof Formulation should suit the mode of administration, and is well within the skill of the art. The invention further relates to pharmaceutical packs and kits comprising one or more containers filled with one or more of the ingredients of the aforementioned compositlons of the invention.

Polypeptides and other compounds of the present invention may be employed alone or in conjunction with other compounds, such as therapeutic compounds.

Preferred forms of systemic admini on of the phaceutical compositions include injection, typically by intravenous injection. Other injection routes, such as subcutaneous, intramuscular, or intraperitoneal, can be used. Alternative means for systemic administration include trarsmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0. 1–100 $\mu$g/kg of subject. Wide variations in the needed dosage, however, are to be expected in view of the variety of compounds available and the differing efficiencies of various routes of adinu aion. For example, oral administration would be expected to require higher dosages than admmtion by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells fromn a subject may be engineered with a polynucleotide, such as a DNA or RNA, to encode a polypeptide ex vivo, and for exarnple, by the use of a retoviral plasmid vector. The cells are then introduced into the subject.

All publications, including but not limited to patents and patent applications, cited in this specification are herein incorporated bv reference as if each individual publication were specifically and individually indicated to be incorporated by reference herein as though fully set forth.

What is claimed is:

1. An isolated polypeptide comprising the amino acid sequence of SEQ ID NO:2.

2. The isolated polypeptide of claim 1 consisting of the amino acid sequence of SEQ ID NO:2.

* * * * *